United States Patent
Wang et al.

(10) Patent No.: US 7,641,786 B2
(45) Date of Patent: Jan. 5, 2010

(54) METHOD OF ANALYZING BASESTOCKS FOR LOW TEMPERATURE PROPERTIES

(75) Inventors: Frank Cheng-Yu Wang, Annandale, NJ (US); Lei Zhang, Vienna, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 183 days.

(21) Appl. No.: 11/667,235

(22) PCT Filed: Nov. 14, 2005

(86) PCT No.: PCT/US2005/041228

§ 371 (c)(1),
(2), (4) Date: Sep. 25, 2007

(87) PCT Pub. No.: WO2006/055502

PCT Pub. Date: May 26, 2006

(65) Prior Publication Data

US 2008/0163672 A1     Jul. 10, 2008

(51) Int. Cl.
*G01N 30/46* (2006.01)
*G01N 30/06* (2006.01)

(52) U.S. Cl. .............. 208/33; 208/18; 208/20; 208/24; 436/33; 436/40; 436/60

(58) Field of Classification Search .......... None
See application file for complete search history.

(56) References Cited

U.S. PATENT DOCUMENTS

| | | | |
|---|---|---|---|
| 5,223,714 A * | 6/1993 | Maggard | 250/343 |
| 5,460,739 A | 10/1995 | Rhodes et al. | |
| 5,699,269 A | 12/1997 | Ashe et al. | |
| 2005/0077208 A1 * | 4/2005 | Miller et al. | 208/18 |
| 2005/0133407 A1 * | 6/2005 | Abernathy et al. | 208/18 |

FOREIGN PATENT DOCUMENTS

WO    WO 2005/054843 A    6/2005

OTHER PUBLICATIONS

Vendeuvre, C. et al - "Comparison of conventional gas chromatography and comprehensive two-dimensional gas chromatography for the detailed analysis of petrochemical samples", Journal of Chromatography, Elsevier Science Publishers B.V. Amsterdam, NL, vol. 1056, No. 1-2, (Nov. 12, 2004), pp. 155-162, XP004627942 ISSN: 0021-9673, abstract p. 155, col. 2, line 4—p. 156, line 26 Figure 3.

(Continued)

*Primary Examiner*—Krishnan S Menon
*Assistant Examiner*—Rebecca Fritchman
(74) *Attorney, Agent, or Firm*—Robert A. Migliorini; Gerard J. Hughes

(57) ABSTRACT

The invention relates to a method for analyzing a lubricating oil for low temperature properties. The method utilizes 2-dimensional gas chromatography (2D GC) to determine the amounts of paraffins and isoparaffins in the oil. In particular, the method analyzes for a particular isoparaffin fraction which is correlated to low temperature performance. The compositional information thus obtained is correlated with formulated oil Mini Rotary Viscometer (MRV) properties.

21 Claims, 6 Drawing Sheets

OTHER PUBLICATIONS

Schoenmakers, P.J. et al—"Comparison of comprehensive two-dimensional gas chromatography and gas chromatography—mass spectrometry for the characterization of complex hydrocarbon mixtures", Journal of Chromatography, Elsevier Science Publishers B.V. Amsterdam, NL, vol. 892, No. 1-2, (Sep. 15, 2000), pp. 29-46, XP004212053, ISSN: 0021-9673, abstract p. 30, col. 1, lines 12-23, p. 31, col. 1, lines 7-17 Figures 1, 2, 7.

Kane, M. et al—"Rheology and structure of waxy crude oils in quiescent and under shearing conditions", Fuel, IPC Science and Technology Press, Guildford, GB, vol. 83, No. 11-12, (Aug. 2004) pp. 1591-1605, XP004508644, ISSN: 0016-2361 abstract.

Vendeuvre, C. et al. -"Characterisation of middle-distillates by comprehensive two-dimensional gas chromatography (GCxGC): A powerful alternative for performing various standard analysis of middle-distillates", Journal of Chromatography A, Elsevier, Amsterdam, NL, vol. 1086, No. 1-2, (Sep. 9, 2005), pp. 21-28, XP004995136, ISSN: 0021-9673 abstract p. 21, col. 2, para. 2—p. 22, col. 1, para. 1—p. 22, col. 2, para. 3, p. 25, col. 1, para. 2—p. 27, col. 2, para. 2, Figures 1, 4-7.

* cited by examiner

METHOD OF ANALYZING BASESTOCKS FOR LOW TEMPERATURE PROPERTIES

FIELD OF THE INVENTION

This invention relates to a method for analyzing a lubricating oil for low temperature properties. The method utilizes 2-dimensional gas chromatography (2D GC) to determine the amounts of paraffins and iso-paraffins in the oil. In particular, the method analyzes for a particular iso-paraffin fraction which is correlated to low temperature performance. The compositional information thus obtained is correlated with formulated oil Mini Rotary Viscometer (MRV) properties.

BACKGROUND OF THE INVENTION

Modern industry standards are placing increasing demands on the low temperature performance of engine oils. The low temperature performance of formulated engine oils can be improved by improving the base oil, by improving the additives used in formulating the oil or both. The low temperature properties of base oils may also be improved by using a synthetic base oil such as a poly-alpha olefin (PAO).

The low temperature properties of any oil are influenced by the presence of waxes such as long chain paraffins. These materials are thought to form wax crystals at low temperatures. These wax materials in turn adversely affect the fluidity of the oil thus causing a deterioration of low temperature properties. It is common practice to at least partially remove waxy materials from basestocks by dewaxing. Dewaxing can be accomplished by either solvent or catalytic means. Solvent dewaxing is a physical method in which waxy molecules are separated based on their solubility properties in select solvents. Catalytic dewaxing chemically converts the waxy molecules to other molecules that have better low temperature properties. Catalytic dewaxing may occur by cracking waxy molecules or by isomerizing waxy molecules.

Another approach typically used in conjunction with dewaxing is the addition of additives such as pour point depressants as part of an additive package added to the lubricating oil basestock to form a formulated oil. Pour point depressants are generally polymeric materials that improve the fluidity of an oil, i.e., they reduce the pour point. However, any given pour point depressant will have a different influence on the pour point depending on the nature of the oil in question. While a given pour point depressant may be effective in one oil, it may be ineffective in another. Thus it is necessary to test the low temperature properties of an oil to know the influence of any given additive package containing a pour point depressant.

One method for determining low temperature pumpability of an engine oil is based on the Mini Rotary Viscometer (MRV). Other means of measuring the low temperature properties of a formulated oil include Brookfield Viscosity, Scanning Brookfield Viscosity, Cold Cranking Simulator test (CCS) and Pour Point. While these test methods may yield information about the low temperature properties of any given oil, they do not necessarily provide information as to the compositional features of that oil.

Various physical techniques have been developed to investigate the composition of crude oils and fractions thereof, including Fourier Transform infrared spectroscopy (FTIR), liquid chromatography, gas chromatography (GC), nuclear magnetic resonance (NMR), and mass spectrometry (MS). Due to the complexity of petroleum mixtures such as crudes, no technique is capable of providing precise compositional details of all the individual molecules making up the petroleum mixture.

GC/MS methods use GC to at least partially separate a mixture into components thereof and MS is then used to identify the components. Petroleum mixtures are very difficult to resolve into individual components due to the complexity of the mixtures and the similar retention times of many individual molecules under given GC conditions.

Two-dimensional gas chromatography (2D GC) is a recent technique that has been developed as a high resolution alternative to conventional GC/MS techniques. In 2D GC, a sample is subjected to two sequential chromatographic separations. The first separation is a partial separation by a first or primary separation column. The partially separated components are then injected into a second or secondary column where they undergo further separation. The two columns usually have different selectivities to achieve the desired degree of separation. An example of 2D GC may be found in U.S. Pat. No. 5,169,039.

It would be desirable if the chromatographic separation information on paraffin distribution in a basestock available from 2D GC could be correlated with low temperature properties of formulated oils.

SUMMARY OF THE INVENTION

This invention relates to a process for predicting the Mini Rotary Viscometer (MRV) properties of a wide range of formulated oils, preferably for use in passenger car internal combustion engines based on paraffin distribution which comprises:

(a) injecting a basestock sample into a first column of a 2-dimensional gas chromatograph, said first column being coated with a non-polar material to separate the basestock sample into a series of first dimension sample components having a first set of retention times;

(b) injecting the separated first dimension sample components from step (a) into a second column coated with a semi-polar material to further separate the separated first dimension sample components into second dimension sample components having a second set of retention times;

(c) subjecting the first and second sets of retention times to qualitative analysis to identify iso-paraffin components or groupings thereof and to quantitative analysis to identify the quantity of the iso-paraffin components having carbon numbers in the lubricant basestock range;

(d) grouping the iso-paraffin components into x groupings where x is a number from 0 to 3 for each identified individual lube paraffins in the carbon number range from 16 to 50;

(e) selecting a lower carbon number n and an upper carbon number m;

(f) identifying a first, second and third iso-paraffin group A, B, and C for each individual carbon number over the range from n to m;

(g) calculating an Isoparaffin Index by the formula:

$$\text{Isoparaffin Index} = \frac{\sum_{L=n}^{m} (IP_A)_L}{\sum_{L=n}^{m} (IP_B)_L + \sum_{L=n}^{m} (IP_C)_L}$$

and;

(h) comparing the calculated Isoparaffin Index to the Isoparaffin Index calculated for standard samples of known MRV wherein the standard samples Isoparaffin Index is a value of about 0.8 or less.

DETAILED DESCRIPTION OF THE INVENTION

Figure 1:
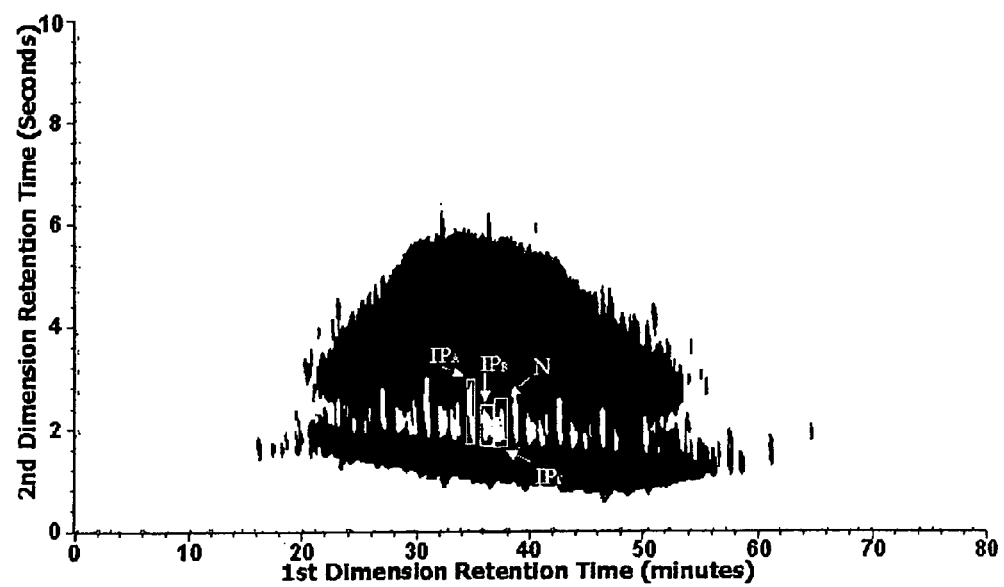
FIG. 1 shows a 2D GC of a typical 130N lube raffinate sample.

The basestocks used to formulate engine oils are typically derived from petroleum distillates having a 10% distillation point greater than 270° C. (518° F.) and a 95% distillation point less than 621° C. (1150° F.) measured by ASTM D 86 or D 2887. Because these distillates frequently contain undesirable quantities of sulfur- and/or nitrogen-containing contaminants they may be solvent extracted, hydrotreated, or both prior to further processing. The terms "baseoil" and "basestock" are used interchangeably herein.

The solvent extraction process selectively dissolves the aromatic components in an extract phase while leaving the more paraffinic components in a raffinate phase. Naphthenes are distributed between the extract and raffinate phases. Typical solvents for solvent extraction include phenol, furfural and N-methyl pyrrolidone. By controlling the solvent to oil ratio, extraction temperature and method of contacting distillate to be extracted with solvent, one can control the degree of separation between the extract and raffinate phases. Sulfur- and nitrogen-containing contaminants are concentrated in the extract phase.

For hydrotreating, the catalysts are those effective for hydrotreating such as catalysts containing Group 6 metals (based on the IUPAC Periodic Table format having Groups from 1 to 18), Groups 8-10 metals, and mixtures thereof. Preferred metals include nickel, tungsten, molybdenum, cobalt and mixtures thereof. These metals or mixtures of metals are typically present as oxides or sulfides on refractory metal oxide supports. The mixture of metals may also be present as bulk metal catalysts wherein the amount of metal is 30 wt. % or greater, based on catalyst. Suitable metal oxide supports include oxides such as silica, alumina, silica-aluminas or titania, preferably alumina. Preferred aluminas are porous aluminas such as gamma or eta. The amount of metals, either individually or in mixtures, ranges from about 0.5 to 35 wt. %, based on the catalyst. In the case of preferred mixtures of groups 9-10 metals with group 6 metals, the groups 9-10 metals are present in amounts of from 0.5 to 5 wt. %, based on catalyst and the group 6 metals are present in amounts of from 5 to 30 wt. %. The amounts of metals may be measured by atomic absorption spectroscopy, inductively coupled plasma-atomic emission spectrometry or other methods specified by ASTM for individual metals.

The acidity of metal oxide supports can be controlled by adding promoters and/or dopants, or by controlling the nature of the metal oxide support, e.g., by controlling the amount of silica incorporated into a silica-alumina support. Examples of promoters and/or dopants include halogen, especially fluorine, phosphorus, boron, yttria, rare-earth oxides and magnesia. Promoters such as halogens generally increase the acidity of metal oxide supports while mildly basic dopants such as yttria or magnesia tend to decrease the acidity of such supports.

Especially preferred metal catalysts include cobalt/molybdenum (1-5 wt % Co as oxide, 10-25 wt % Mo as oxide), nickel/molybdenum (1-5 wt % Ni as oxide, 10-25% Co as oxide), or nickel/tungsten (1-5 wt % Ni as oxide, 10-30 wt % W as oxide) on alumina.

Hydrotreating conditions include temperatures of from 150 to 400° C., preferably 200 to 350° C., a hydrogen partial pressure of from 1480 to 20786 kPa (200 to 3000 psig), preferably 2859 to 13891 kPa (400 to 2000 psig), a space velocity of from 0.1 to 10 LHSV, preferably 0.1 to 5 LHSV, and a hydrogen to feed ratio of from 89 to 1780 $m^3/m^3$ (500 to 10000 scf/B), preferably 178 to 890 $m^3/m^3$.

The hydrotreated basestock may be passed directly to a dewaxing step or preferably, stripped to remove gaseous contaminants such as hydrogen sulfide and ammonia prior to dewaxing. Stripping can be by conventional means such as flash drums or fractionators.

Dewaxing

Dewaxing is one method used to control the low temperature properties of basestocks. It is generally accepted that waxy molecules such as long chain paraffins crystallize at low temperatures thereby adversely impacting cold flow properties. Thus the removal of waxy molecules from the basestock is considered to improve the basestocks low temperature properties. Two commonly employed methods of removing waxy molecules from basestocks are solvent dewaxing, catalytic dewaxing or a combination of solvent and catalytic dewaxing. Trim dewaxing is solvent dewaxing followed by catalytic dewaxing.

For solvent dewaxing, the dewaxing solvent used may include the $C_3$-$C_6$ ketones such as methyl ethyl ketone (MEK), methyl isobutyl ketone (MIBK), mixtures of MEK and MIBK, aromatic hydrocarbons like toluene, mixtures of ketones and aromatics like MEK/toluene, ethers such as methyl t-butyl ethers and mixtures of same with ketones or aromatics. Similarly, liquefied, normally gaseous hydrocarbons like propane, propylene, butane, butylene, and combinations thereof may be used as the solvent. Preferably the solvent employed will be a mixture of methyl ethyl ketone and methyl isobutyl ketone.

The solvent dewaxing process typically involves mixing the lube oil boiling range feedstock with a dewaxing solvent at atmospheric pressure, separating precipitated wax and recovering solvent for recycling. The lube oil boiling range feedstock is mixed with chilled solvent to form an oil-solvent solution and precipitated wax is thereafter separated by, for example filtration. The temperature and solvent are selected so that the oil is dissolved by the chilled solvent while the wax is precipitated.

A particularly suitable solvent dewaxing process involves the use of a cooling tower where solvent is prechilled and added incrementally at several points along the height of the cooling tower. The lube oil boiling range feedstream-solvent mixture is agitated during the chilling step to permit substantially instantaneous mixing of the prechilled solvent with the lube oil boiling range feedstream. The prechilled solvent is added incrementally along the length of the cooling tower so as to maintain an average chilling rate at or below 10° F./minute, usually between about 1 to about 5° F./minute. The final temperature of the lube oil boiling range feedstream-solvent/precipitated wax mixture in the cooling tower will usually be between 0 and 50° F. (−17.8 to 10° C.). The mixture may then be sent to a scraped surface chiller to separate precipitated wax from the mixture.

As stated above, the solvent dewaxing of the lube oil boiling range feedstream occurs under effective solvent dewaxing conditions. Effective solvent dewaxing conditions are to be considered those solvent dewaxing conditions that are capable of removing at least a portion of the wax contained in the lube oil boiling range feedstream. Generally, effective solvent dewaxing conditions will include that amount of solvent that when added to the lube oil boiling range feedstream will be sufficient to provide a liquid/solid weight ratio of about 5/1 to about 20/1 at the dewaxing temperature and a solvent/oil volume ratio between 1.5/1 to 5/1. The solvent dewaxing of the lube oil boiling range feedstream typically results in a partially dewaxed fraction having a pour point from about +30° C. to about −20° C.

Catalytic dewaxing usually involves one or both the following mechanisms: catalytic dewaxing by cracking waxy molecules or catalytic dewaxing by isomerizing waxy molecules. Catalytic dewaxing by cracking involves molecular weight reduction since waxy molecules are cracked to lower molecular weight molecules. Catalytic dewaxing by isomerization involves isomerizing waxy molecules (straight chain paraffins) to branched chain paraffins. It should be noted that very few if any dewaxing catalysts operate exclusively by one mechanism.

Catalysts for dewaxing by catalytic cracking include ZSM-5, ZSM-11, ZSM-22, ZSM-35, mordenite and beta. Since this form of dewaxing involves cracking waxy molecules, some yield loss may occur. Dewaxing catalysts may be characterized by their alpha values. The alpha value of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in the Journal of Catalysis, 4, 522-529 (1965); 6, 278 (1966); and 61, 395 (1980), each incorporated herein by reference. Catalysts employed for dewaxing by catalytic cracking can have an alpha value greater than 100, preferably 100 to 180. The alpha value of a catalyst may be increased by initially treating the catalyst with nitric acid or by mild steaming as discussed in U.S. Pat. No. 4,326,994. Steaming is a means of adjusting the silica:alumina ratio of the catalyst and hence its alpha value.

Catalysts for dewaxing by isomerization are those which isomerize at least a portion of the waxy n-paraffin molecules to isoparaffins. Waxy molecules may be from a mineral source, synthetic source or a mixture of the two, e.g., Fischer Tropsch wax. Such isomerization catalysts minimize the amount of dewaxing by cracking mechanisms. Because there is little molecular weight reduction associated with isomerizing catalysts, there is less yield loss as compared to dewaxing by cracking. Isomerizing dewaxing catalysts are typically metal loaded with Group 6 metals, Group 8-10 metals and mixtures thereof (based on the IUPAC format). Especially preferred metals are Groups 8-10 noble metals, especially Pt, Pd or mixtures thereof. These metals are loaded at the rate of 0.1 to 30 wt % based on catalyst.

Hydrodewaxing catalysts suitable for use herein may be either crystalline or amorphous. Amorphous hydrodewaxing catalysts include alumina, fluorided alumina, silica-alumina, and fluorided silica-alumina. Such catalysts are well known. Crystalline materials are molecular sieves that contain at least one 10 or 12 ring channel and may be based on aluminosilicates (zeolites) or on aluminophosphates such as silicoaluminophosphates (SAPO's) and magnealuminophosphates (MAPOs). Molecular sieves suitable for use herein contain at least one 10 or 12 channel. Examples of such zeolites include ZSM-22, ZSM-23, ZSM-35, ZSM-48, ZSM-57, ferrierite, ITQ-13, MCM-68 and MCM-71. Examples of aluminophosphates containing at least one 10 ring channel include ECR-42, SAPO-11, SAPO-31 and SAPO-41. Examples of molecular sieves containing 12 ring channels include zeolite beta, and MCM-68.

The molecular sieves are typically composited with binder materials that are resistant to high temperatures and that may be employed under hydrodewaxing conditions to form a finished hydrodewaxing catalyst or may be binderless (self bound). The binder materials are usually inorganic oxides such as silica, alumina, silica-aluminas, binary combinations of silicas with other metal oxides such as titania, magnesia, thoria, zirconia and the like and tertiary combinations of these oxides such as silica-alumina-thoria and silica-alumina magnesia. The preferred binder is alumina. The amount of molecular sieve in the finished hydrodewaxing catalyst is from 10 to 100, preferably 35 to 100 wt. %, based on catalyst. Such catalysts are formed by methods such spray drying, extrusion and the like. The hydrodewaxing catalyst may be used in the sulfided or unsulfided form, and is preferably in the sulfided form.

Effective hydrodewaxing conditions as used herein includes temperatures between about 200° C. to about 400° C., preferably about 225° C. to about 350° C., more preferably 250 to 310° C., pressures between about 2860 to about 20786 kPa (about 400 to about 3000 psig), preferably about 4238 to about 17338 kPa (about 600 to about 2500 psig), more preferably about 4238 to about 10443 kPa (about 600 to about 1500 psig) hydrogen treat gas rates of about 89 to about 890 m$^3$/m$^3$ (about 500 to about 5,000 SCF H$_2$/B), preferably about 107 to about 445 m$^3$/m$^3$ (about 600 to about 2500 SCF H$_2$/B), and liquid hourly space velocities ("LHSV") of about 0.1 to about 10 V/V/hr, preferably about 0.1 to about 5 V/V/hr, more preferably about 0.5 to about 2 V/V/hr.

Formulated Oils

The properties of formulated oils, particularly the low temperatures properties, are a function of the basestock and the additive package used to prepare the formulated oil. As noted above, the low temperature properties, e.g., the pour point, Brookfield viscosity, MRV, cold cracking simulator test (CCS) and gel index, of a basestock are adversely affected by waxes. Thus it is advantageous to remove at least some of the waxy components of the basestock by dewaxing. The viscosity index of the oil is likewise impacted by basestock components. The VI is adversely impacted by components such as aromatics which have a low VI. The low temperatures properties are also affected by whether the basestock itself is synthetic such as PAO or of mineral origin.

The MRV of a formulated baseoil is an indicator of low temperature properties. The MRV is measured by standards tests such as ASTM D 3829 and D 4684. The MRV test measures the pumping performance of a formulated baseoil at low temperature. Smaller values of MRV correlate with better low temperature properties Another factor influencing the properties of the formulated oil is the additive package (adpak) used to formulate the oil. Additive packages contain at least one component selected from dispersants, detergents, wear inhibitors, antioxidants, rust inhibitors, demulsifiers, extreme pressure agents, friction modifiers, multifunction additives, viscosity index improvers, pour point depressants, and foam inhibitors.

Many different additive packages are commercially available. The precise formulations vary depending on the manufacturer and the intended use of the engine oil. For example, engine oils for diesel engines may contain different additive components as compared to engine oils for gasoline powered engines. Formulations for hot climates will vary from those for cold climates.

Two-Dimensional Gas Chromatography

2D GC is an alternative to gas chromatography/mass spectrometry. In 2D GC, a sample is injected into a first column and the separated components injected into a second column in series with the first.

A sample is injected into an inlet device connected to the inlet of a first column to produce a first dimension chromatogram. Sample injection may be by any known sample injection device such as a syringe. The inlet device may hold a single sample or may hold multiple samples for injection into the first column. The column contains a stationary phase that is usually the column coating material.

The first column may be coated with a non-polar material. When the column coating material is methyl silicon polymer, the polarity can be measured by the percentage of methyl group substituted by the phenyl group. The polarity of coating materials are measured on a % of phenyl group substitution scale from 0 to 100 with zero being non-polar and 80 (80% phenyl substitution) being considered as polar. These methyl silicon polymers are considered non-polar and have polarity values in the range from 0 to 20. Phenyl substituted methyl silicon polymers are considered semi-polar and have polarity values of 21 to 50. Phenyl substituted methyl silicon polymers coating materials have been called polar materials when greater than 50% phenyl substitution group is included in polymers. Other polar coating polymers, such as carbowaxes, were also used in chromatographic applications. Carbowaxes are high molecular weight polyethylene glycols. In addition, a series of carborane silicon polymers sold under the trade name Dexsil have been especially designed for high temperature applications.

The first column coated with a non-polar material provides a first separation of the sample. The first separation, also known as the first dimension, generates a series of bands over a given time period. This first dimension chromatograms is not unlike the chromatogram that could be obtained from a conventional chromatogram. The bands represent individual components or groups of components of the sample injected, and separated or partially overlapping with adjacent bands.

When the complex mixture is separated by the first dimension column, it still suffers many co-elutions that are not able to be separated by the first dimension column. The bands of separated materials from the first dimension are then sent in their entirety to the second column to perform a further separation, especially of the co-eluted components. This further separation is referred to as a second dimension. The second dimension is a second column coated with a semi-polar or polar material, preferably a semi-polar coating material.

In order to make the data acquisition as well as the detector signal meaningful, a modulator is required to manage the flow between the end of the first column and the beginning of the second column. Modulators may be thermal modulators that use a trap/release mechanism. In this mechanism, cold nitrogen gas is used to trap separated sample from the first dimension followed by a periodic pulse of hot nitrogen to release trapped sample to a second dimension. Each pulse is analogous to a sample injection into the second dimension.

The role of the modulator is (1) collect the continuous eluent flow out from the end of the first column with a fixed period of time (modulated period), and (2) inject collected eluent to the beginning of the second column by releasing collected eluent at the end of modulated period. The function of the modulator is (1) define the beginning time of a specific second dimensional column separation and (2) define the length of the second dimensional separation (modulation period).

The separated bands from the second dimension are coupled with the bands from the first dimension to form a comprehensive 2D chromatogram. The bands are placed in a retention plane wherein the first dimension retention times and the second dimension retention times form the axes of the 2D chromatogram.

For example, a conventional GC experiment takes 80 minutes to separate a mixture (a chromatogram with 80 minutes retention time, x-axis). When the same experiment is performed under 2D GC conditions with a 10 second modulation period, it will become 480 chromatograms (60 seconds×80 minutes divided 10 seconds) where each 10 second chromatogram (y-axis) lines up one-by-one along the retention time axis (x-axis). In 2D GC, the x-axis is the first dimension retention time (the same as conventional GC), the y-axis is the second dimensional retention time, the peak intensity should stick out in the third dimension z-axis. In order to express this 3D picture on two dimensional paper, the intensity has been converted based on a pre-defined gray scale table to express their relative peak intensity by gray-scale.

FIG. 1 shows a 2D GC chromatogram of a typical 130N lube raffinate sample. In this 2D GC/FID (flame ionization detector) run, data point from the experiment dimension is 480×1000. The display dimension is: 2880×2000. Separation column set used is: 1st Column, SGE BPX-5 (BPX is a phenyl siloxane polymer), 30 meter, 0.25 mmID, 1.0 μm Film and 2nd Column, SGE BPX-50, 9.0 meter, 0.25 mmID, 0.25 μm Film. Oven temperature program was set at 210° C. for 0 minutes and ramped at 1.5° C. per minute to 315° C. for 10 minutes. Flow program is 1.5 ml per minute for 0 minute and increased 0.05 ml/minute per minute to 5.0 ml per minute for 0 minute. The inlet temperature was set at 300° C. with split/splitness ratio of 75:1. The sample injection volume is 0.2 μl.

To determine the Isoparaffin Index, all paraffin components in the baseoil are identified in the carbon number range from 16 to 50. The Isoparaffin Index is calculated over a given carbon range bounded by a lower carbon number, n, and an upper carbon number, m, For example, the lower carbon value can be selected as n=23 and an upper carbon value as m=31 for 130N lube raffinate sample. Because the resolution is not sufficient to identify individual isoparaffins, the isoparaffins are formed into groups. At a given carbon number L, the isoparaffins for that carbon number are grouped into discrete groups, preferably 3 groups denoted as $(IP_A)_L$, $(IP_B)_L$, and $(IP_C)_L$. The process is repeated for each carbon number over the entire carbon number range from n to m in the 2D GC spectrum. The peak volume of each normal paraffin component and isoparaffin groups is integrated to obtain the weight percentage of a specific component to the total sample. In the 2D GC chromatogram of 130N lubricant raffinate, shown in FIG. 1, the calculation is performed from carbon number of 23 to 31 ($C_{23}$ to $C_{31}$). The individual component composition is summarized in the following Table 1.

TABLE 1

130N Lube Raffinate Composition Based on 2D-GC Chromatogram

| Carbon Number | 23 | 24 | 25 | 26 | 27 | 28 | 29 | 30 | 31 |
|---|---|---|---|---|---|---|---|---|---|
| N | 0.98 | 2.10 | 3.58 | 3.66 | 3.36 | 2.60 | 1.89 | 1.11 | 0.57 |
| $IP_A$ | 0.16 | 0.47 | 1.33 | 1.70 | 1.86 | 1.52 | 1.18 | 0.88 | 0.57 |
| $IP_B$ | 0.31 | 0.85 | 1.61 | 1.82 | 1.70 | 1.50 | 1.18 | 0.75 | 0.35 |
| $IP_C$ | 0.08 | 0.16 | 0.38 | 0.44 | 0.35 | 0.40 | 0.27 | 0.16 | 0.06 |

N is the amount of normal paraffin at each individual carbon number but this is not needed to calculate the Isoparaffin Index. For any given sample, the Isoparaffin Index is calculated as the ratio of the sum of Isoparaffins A over the range of carbon number from n to m to the sum of Isoparaffins B plus C over the range of carbon number from n to m. This is represented by the following Equation 1:

$$\text{Isoparaffin Index} = \frac{\sum_{L=n}^{m}(IP_A)_L}{\sum_{L=n}^{m}(IP_B)_L + \sum_{L=n}^{m}(IP_C)_L} \quad (1)$$

In the above equation, n is a lower carbon number in the range 16 to 50, m is the upper carbon number in the range 16 to 50, $(IP)_L$ is the amount of iso-paraffins in wt. % for each individual carbon number L. The subscripts A, B and C represent the different groups of iso-paraffins from the Table 1 above. For the data in Table 1, n=23 and m=31, $$\sum_{L=23}^{31}(IP_A)_L \text{ is } 9.67, \sum_{L=23}^{31}(IP_B)_L$$

is 10.07 and $$\sum_{L=23}^{31}(IP_C)_L$$

is 2.30. The Isoparaffin Index is calculated as 9.67/(10.03+2.30) or 0.78.

The process of gathering data shown in FIG. 1 and Table 1 above is repeated for a set of standard non-formulated samples. For purposes of calculating the Isoparaffin Index, the sample may be formulated or non-formulated since the Isoparaffin Index is independent of the adpak used to formulate the samples. On the other hand, the MRV for each sample is measured on a formulated sample since the MRV is influenced by the adpak used to formulate the sample, and the Isoparaffin Index is calculated based on the 2D GC analysis.

The same adpak is used to formulate each sample. A commercial additive package for GF-3 engine oils was used to make the formulated oil. This package contains a detergent/inhibitor package, a viscosity modifier, and a pour point depressant. The results for a series of samples having different calculated Isoparaffin indexes and corresponding MRVs are plotted in FIG. 2 which is a graph with measured MRV being the Y-axis and Isoparaffin Index being the X-axis for the set of samples.

Figure 2:
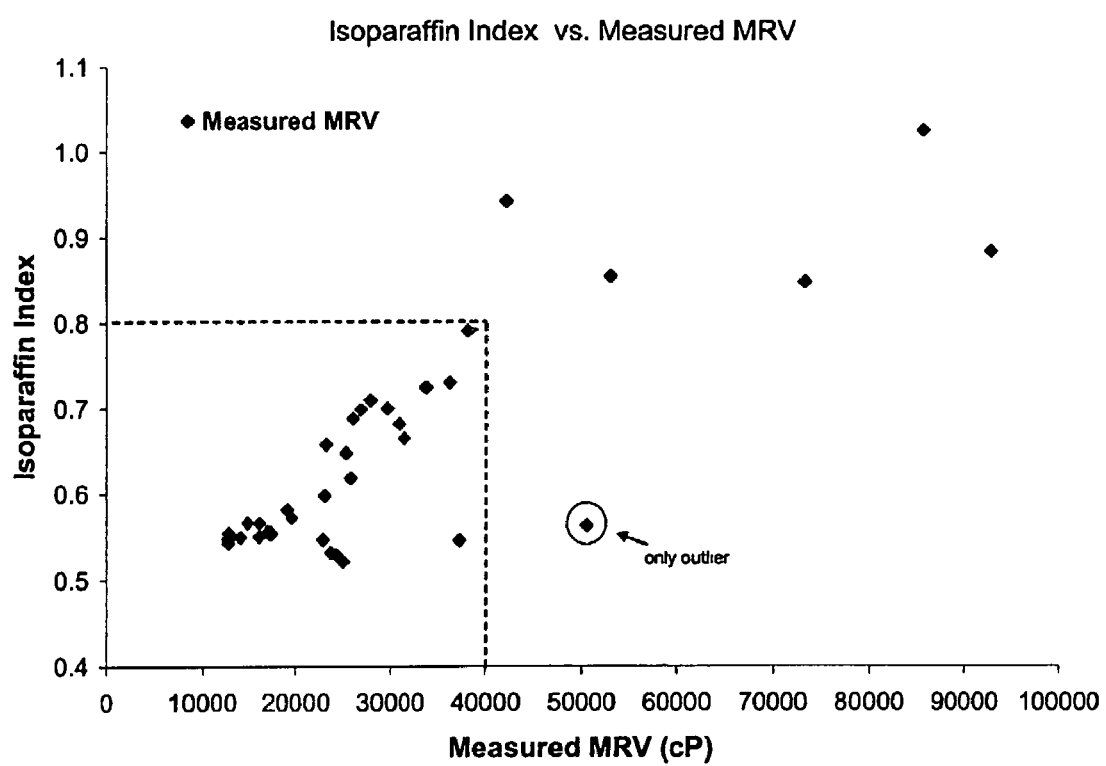
FIG. 2 is a graph showing a plot of measured formulated baseoil MRV versus Isoparaffin Index for a series of samples having different calculated Isoparaffin Indexes.

As can be seen from FIG. 2, if the desired formulated baseoil MRV is 40000 cP, then the target Isoparaffin Index is 0.8. For any given sample of formulated oil, if the Isoparaffin Index for the base oil is less than 0.8, then it can be formulated into an oil having a MRV of 40000 cP or less.

The traditional MRV measurement requires large amount of a finished lubricating oil, such as but not limited to, an engine oil sample (150 to 200 ml) and also needs long test periods (>45 hrs) at low temperature between −10 and −40° C. In many instances, the viscometric properties of baseoil cannot translate into the low temperature flow property of formulated engine oil. It is highly desirable to develop an analytic tool that can precisely predict a basestock's formulated PCMO low temperature performance in a rapid test. The precise MRV prediction using advance 2D GC technique can dramatically reduce the time and cost related to the conventional MRV test.

This invention may be further understood by reference to the following non-limiting examples.

EXAMPLES

The following Examples are directed to demonstrating the impact of Isoparaffin Index evaluation on basestocks produced using various processing schemes. The Isoparaffin Index is correlated to measured MRV for these basestocks. First, solvent dewaxing ("SDW") followed by catalytic dewaxing ("HDW") was applied to a commercially available basestock to improve the low temperature performance. Then a more in-depth dewaxing evaluation was completed on light basestock ("LBS") 130N raffinate to focus on the impact on low temperature performance from formulating engine oils with basestocks produced from varying dewaxing process schemes. Basestocks were produced by dewaxing through two different dewaxing schemes, which combined both HDW and SDW to different extents. One case focused on partially solvent dewaxing to an intermediate pour point followed by HDW to the final target pour point, in order to preserve wax production. Another focused on partially HDW to an intermediate pour point followed by SDW to the final target pour point. The Isoparaffin Index allowed the evaluation of the basestocks to predict which would better from the standpoint of formulated oil MRV.

Example 1

A commercially solvent dewaxed basestock was used as the feed in trim dewaxing (SDW followed by HDW) experiments. The commercial basestock is a mixture of light basestock at approximately 81 wt % and medium basestock at approximately 19 wt %. A 130N lube raffinate was used as the feed in the two combined dewaxing schemes. The basestock properties are summarized in Table 2.

TABLE 2

Commercial Basestock and 130N Raffinate Properties

| Feed Description | Commercial basestock | 130N Lube Raffinate |
|---|---|---|
| Sample Used in Pilot Unit/Run | Trim HDW | SDW -> HDW<br>HDW -> SDW |
| Cloud Point (° C.) | — | 35.6 |
| Pour Point (° C.) | −18 | 31 |
| Density @ 15° C. (g/cc) | 0.844 | 0.8332 |
| Sulfur (wppm) | <10 | <1 |
| Nitrogen (wppm) | <1 | <0.3 |
| Color (Lovibond Saybolt) | >+30 | >+30 |
| RI @ 75° C. | — | 1.4401 |
| KV @ 40° C. (cSt) | 23.3 | 16.910 |
| KV @ 100° C. (cSt) | 4.6 | 3.972 |
| VI | 114 | 135.1 |
| Wax Content (%) | — | 25.3 |
| MRV (cP) | 36211 | — |

Example 2

All HDW work in three process methods used commercially available Pt/ZSM-48 as the dewaxing catalyst. The commercial 1/16" quadrulobe extrudates contain 65% ZSM-48 crystals bound with 35% alumina. Platinum was impregnated onto the extrudates using platinum tetraammine nitrate.

HDW Procedure

The HDW studies were performed using a continuous catalyst testing unit, which consists of a liquid feed system with an ISCO syringe pump, a fixed-bed tubular reactor with a three-zone furnace, liquid product collection, and an on-line MTI GC for gas analysis. Typically, 5-10 cc of catalyst was sized to 14/20 mesh and charged in an up-flow 3/8"stainless steel reactor containing a 1/8" thermowell. After the unit was pressure tested, the catalyst was dried at 300° C. for 2 hours with 250 cc/min $N_2$ at ambient pressure. If pre-sulfidation of the catalyst was required, 2% $H_2S$ in hydrogen was flowed through the catalyst bed at 100 sccm for 1 hour. Upon completion of the catalyst treatment, the reactor was cooled to 150° C., the unit pressure was set to 1000 psig by adjusting the Mity-Mite back-pressure regulator and the gas flow was switched from $N_2$ to $H_2$. Liquid feedstock was introduced into the reactor at the desired liquid hourly space velocity (LHSV). Once the liquid feed reached the downstream knockout pot, the reactor temperature was increased to the target value. A material balance (MB) was initiated until the unit was lined out for 6 hours. The total liquid product (TLP) was collected in the MB dropout pot. Gas samples were analyzed with an on-line HP MTI gas chromatograph (GC) equipped with both TCD and FID detectors. A series of runs were performed to understand the catalyst activity/product properties as function of the process variables, such as LHSV and process temperature. The TLP product from each balance was cut at 370° C. by batch distillation. The properties of the 370° C.+ dewaxed oil were analyzed.

SDW Lab Procedure

The lab solvent dewaxings were conducted using a single stage batch filtration with the large Buchner funnel apparatus. This apparatus uses a 24-cm filtration area and has up to a 1.5 gallon oil/wax/solvent slurry capacity. The solvent was a mixture of methyl ethyl ketone (MEK) and methyl isobutyl ketone (MIBK).

As the filtration proceeds, the predominately wax component is left on the surface of the filtration media, with the filtrate (oil and solvent) passing through the filter into a collection flask. These two products are then stripped of their respective solvents using a rotary vacuum stripper to complete the filtration process. The DWO and wax were further analyzed to determine their individual physical properties.

The feed and basestock produced as described above were then blended to make a 5W-30 passenger car motor oil (PCMO). The above basestock was a lighter viscosity than required for the finished 5W-30 oil and hence a second basestock which was somewhat heavier was added to all the blends to hit a base oil desired viscosity target. A commercial additive package for GF-3 engine oils was then added to make the formulated oil. This package consists of a detergent/inhibitor package, a viscosity modifier, and a pour point depressant. The package utilized and the second basestock were constants in all the blends, only the light basestock was varied. The formulated oils were tested for cold flow property with a mini rotary viscometer (MRV), according to the ASTM D4684 method.

Example 3

2D GC Measurement of Baseoil Composition

The 2D GC (GC×GC) system consists of an Agilent 6890 gas chromatograph (Agilent Technology, Wilmington, DE) configured with inlet, columns, and detectors. A split/splitless inlet system with an eight-vial tray autosampler was used. The two-dimensional capillary column system utilizes a non-polar first column (BPX-5, 30 meter, 0.25 mm I.D., 1.0 µm film), and a polar (BPX-50, 9 meter, 0.25 mm I.D., 0.25 µm film), second column. Both capillary columns are the products of SGE Inc. Austin, Tex. A dual jet thermal modulation assembly based on Zoex technology (Zoex Corp. Lincoln, Neb.) which is liquid nitrogen cooled "trap-release" dual jet thermal modulator is installed between these two columns. A flame ionization detector (FID) is used for the signal detection. A 0.2 microliter sample was injected with 75:1 split at 300° C. from Inlet. Carrier gas is programmed from 1.5 ml/min with 0 minute hold and 0.05 ml/min per minute increment to 5.0 ml/min with 0 minute hold. The oven was programmed from 210° C. with 0 minute hold and 1.5° C. per minute increment to 315° C. with 0 minute hold. The total GC run time was 70 minutes. The modulation period was 10 seconds. The sampling rate for the detector was 100 Hz. After data acquisition, it was processed for qualitative and quantitative analysis. The qualitative analysis converted data to a two-dimensional image that was processed by a commercial program, "Transform" (Research Systems Inc., Boulder, Colo.). The two-dimensional image was further treated by "PhotoShop" program (Adobe System Inc., San Jose, Calif.) to generate publication-ready images. An in-house program was used to quantify the peak volumes.

Figure 3:
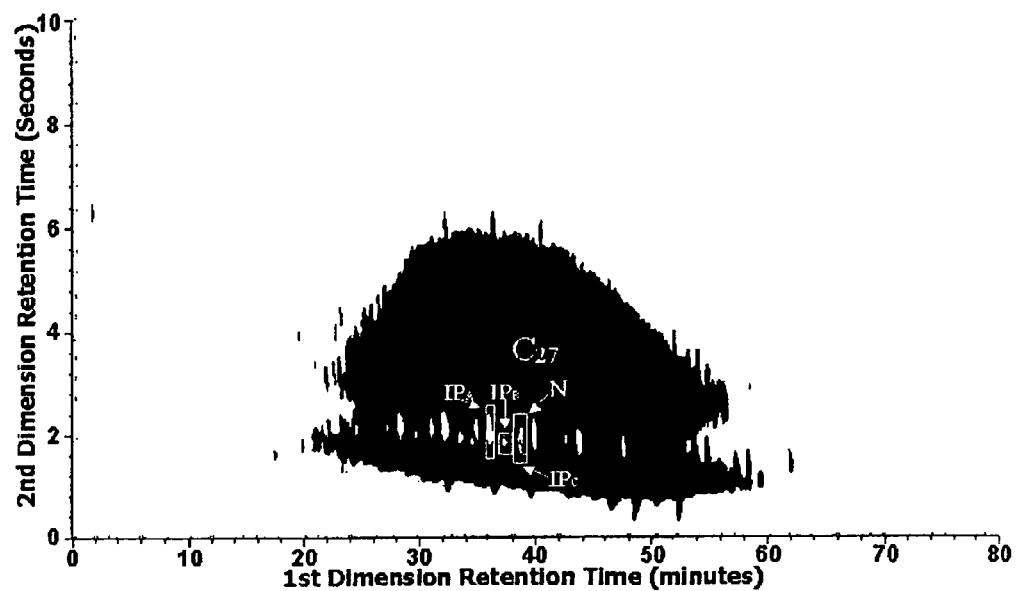
FIG. 3 presents a typical 2D GC (GC×GC) chromatogram of commercial basestock used as feedstock.

FIG. 3 presents a 2D GC (GC×GC) chromatogram of the commercial solvent dewaxed basestock described Example 1. Using $C_{27}$ as an example, the chromatogram demonstrates the detailed n-paraffins (N) and iso-paraffins (IP) identifications and selected integration volumes of identified components. Since all iso-paraffins are not completely resolved in the two-dimensional space, the iso-paraffins have been grouped into three regions, $IP_A$, $IP_B$, and $IP_C$, at each associated carbon number of the baseoil components. While integrating the identified peaks through the entire retention time of the 2D GC chromatogram (in the range of $C_{23}$ to $C_{31}$), the weight percentage of n-paraffin and iso-paraffins at each associated carbon number can be quantitatively obtained.

Table 3 shows a typical weight percentage of n-paraffins and iso-paraffins at each associated carbon numbers in the commercial feed

TABLE 3

COMMERCIAL FEEDSTOCK
PP = −18° C.
MRV = 36211 cP

| Carbon Number | 23 | 24 | 25 | 26 | 27 | 28 | 29 | 30 | 31 |
|---|---|---|---|---|---|---|---|---|---|
| N | 0.27 | 0.66 | 0.95 | 0.84 | 1.00 | 0.79 | 0.51 | 0.41 | 0.28 |
| $IP_A$ | 0.14 | 0.66 | 1.34 | 1.76 | 1.88 | 1.62 | 1.30 | 1.04 | 0.68 |
| $IP_B$ | 0.42 | 0.89 | 1.46 | 1.52 | 1.71 | 1.52 | 1.16 | 0.79 | 0.54 |
| $IP_C$ | 0.09 | 0.26 | 0.65 | 1.02 | 0.62 | 0.58 | 0.42 | 0.32 | 0.22 |

Example 4

This Example defines a baseoil (basestock) composition with superior LTP. A comparison was made between basestocks produced from the combinations of commercial SDW and HDW processes (using Pt/ ZSM-48). The upstream dewaxing process (SDW or HDW) dewaxed the feed to a pour point in the range of about −16 to about −20° C. The downstream process (HDW or SDW) completed the dewaxing to the target pour point. For formulated engine oils containing basestocks made this way (SDW followed by HDW), it a significant improvement in formulated engine oil low temperature performance was achieved, as measured by MRV for formulated engine. In contrast, if the base oil were made by HDW to an intermediate pour point followed by SDW to a target point, formulated engine oils containing such a basestock did not show an improvement in low temperature performance as measured by MRV.

The commercial SDW basestock at a −18° C. pour point, when formulated engine into a 5W-30 engine oil, achieved an MRV measurement of ~36,211 cP. The molecular structural composition was calculated based on 2D GC analysis and summarized in Table 3.

Trim HDW produced the basestocks, which when formulated into a 5W-30 engine oil, demonstrated the largest improvement in cold flow performance as measured by MRV reduction for a given pour point. For examples, trim catalytic hydrodewaxing to about −19 ° C. pour point is effective in lowering the MRV from 36,211 cP to an average value of 19,536 cP, a 46% reduction in MRV apparent viscosity. When comparing to commercial feed, we clearly see that the $IP_A$ concentration at each carbon number decreased (Table 4).

TABLE 4

Trim HDW ZSM-48
PP = −19° C.
MRV = 19536 cP
Rxn Temp 290° C.

| Carbon Number | 23 | 24 | 25 | 26 | 27 | 28 | 29 | 30 | 31 |
|---|---|---|---|---|---|---|---|---|---|
| N | 0.31 | 0.71 | 0.98 | 0.86 | 1.01 | 0.79 | 0.50 | 0.40 | 0.28 |
| $IP_A$ | 0.14 | 0.61 | 1.16 | 1.46 | 1.60 | 1.35 | 1.07 | 0.88 | 0.57 |
| $IP_B$ | 0.49 | 1.03 | 1.63 | 1.68 | 1.89 | 1.63 | 1.24 | 0.83 | 0.56 |
| $IP_C$ | 0.12 | 0.28 | 0.69 | 1.08 | 0.66 | 0.60 | 0.44 | 0.32 | 0.22 |

Figure 4:
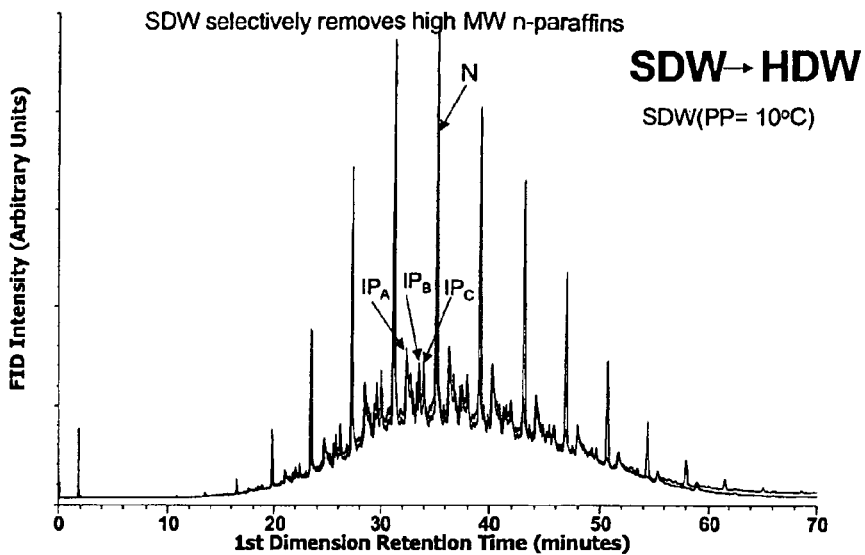
FIG. 4 are GC chromatograms illustrating the compositional changes in n-paraffin, $IP_A$, $IP_B$, and $IP_C$ regions for SDW->HDW sample.
Figure 4:
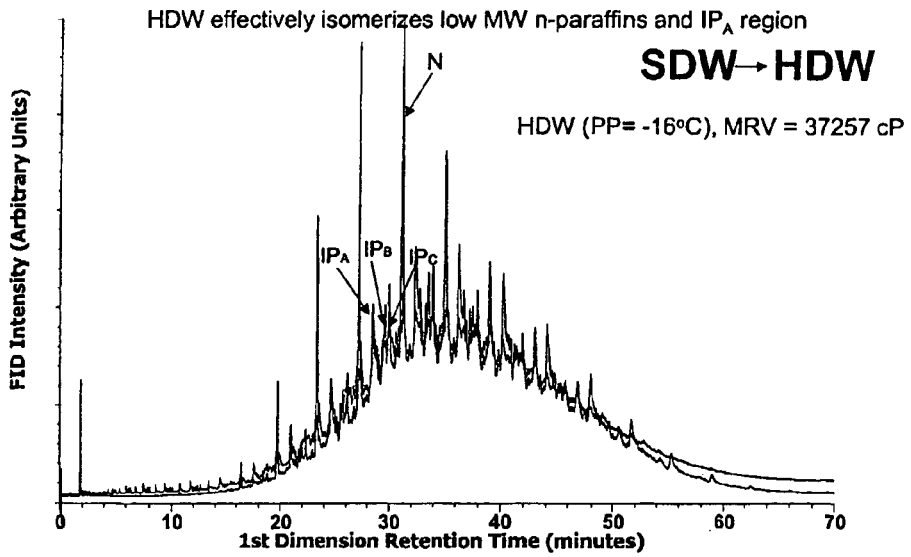

Engine oils formulated with the SDW→HDW basestocks also showed significant improvement in MRV in comparison to the full SDW basestock. 2D GC compositional analysis presented the different molecular structures of the intermediate dewaxed products and how the final dewaxing stage removes the remaining wax from the intermediate products. SDW typically first removes high molecular weight waxy paraffins based on physical separation. In contrast, the HDW process converts waxy hydrocarbon molecules to isomerates using bifunctional catalysts. In the case of SDW→HDW, the waxy feed was SDW in the first step to an intermediate pour point by reducing the heavy end waxy molecules. As shown by gas chromatography, the initial SDW process selectively removes the heavier molecular weight n-paraffin. The following HDW process effectively isomerizes n-paraffins and iso-paraffin to achieve the desired lube properties. The detailed molecular compositions at each process stage are presented in FIG. 4 and Tables 5-7. FIG. 4 are GC chromatograms illustrating the compositional changes in n-paraffin, $IP_A$, $IP_B$, and $IP_C$ regions for SDW->HDW sample. Table 5 shows a raffinate feed and n-Paraffins and iso-paraffins distribution based on the each identified carbon number in the lube raffinate feed. Table 6 and 7 show the SDW intermediate and the SDW-HDW product: the n-Paraffins and iso-paraffins distribution based on the each identified carbon number.

TABLE 5

130N Lube Raffinate
PP = 30° C.
MRV = N/A

| Carbon Number | 23 | 24 | 25 | 26 | 27 | 28 | 29 | 30 | 31 |
|---|---|---|---|---|---|---|---|---|---|
| N | 0.98 | 2.10 | 3.58 | 3.66 | 3.36 | 2.60 | 1.89 | 1.11 | 0.57 |
| $IP_A$ | 0.16 | 0.47 | 1.33 | 1.70 | 1.86 | 1.52 | 1.18 | 0.88 | 0.57 |
| $IP_B$ | 0.31 | 0.85 | 1.61 | 1.82 | 1.70 | 1.50 | 1.18 | 0.75 | 0.35 |
| $IP_C$ | 0.08 | 0.16 | 0.38 | 0.44 | 0.35 | 0.40 | 0.27 | 0.16 | 0.06 |

Total: 41.88

TABLE 6

SDW
PP = 10° C.
MRV = N/A

| Carbon Number | 23 | 24 | 25 | 26 | 27 | 28 | 29 | 30 | 31 |
|---|---|---|---|---|---|---|---|---|---|
| N | 1.02 | 1.82 | 2.63 | 2.02 | 1.69 | 1.08 | 0.70 | 0.38 | 0.18 |
| $IP_A$ | 0.18 | 0.59 | 1.61 | 2.00 | 2.18 | 1.77 | 1.36 | 0.94 | 0.61 |
| $IP_B$ | 0.35 | 1.01 | 1.89 | 2.05 | 1.89 | 1.56 | 1.11 | 0.65 | 0.29 |
| $IP_C$ | 0.07 | 0.14 | 0.45 | 0.50 | 0.42 | 0.47 | 0.29 | 0.17 | 0.07 |

Total: 36.13

TABLE 7

SDW → HDW
PP = −16° C.
MRV = 37257 cP
Rxn Temp = 310° C.

| Carbon Number | 23 | 24 | 25 | 26 | 27 | 28 | 29 | 30 | 31 |
|---|---|---|---|---|---|---|---|---|---|
| N | 0.66 | 1.20 | 1.46 | 1.19 | 1.29 | 0.91 | 0.48 | 0.34 | 0.19 |
| $IP_A$ | 0.58 | 1.14 | 1.71 | 1.94 | 2.01 | 1.58 | 1.18 | 0.82 | 0.46 |
| $IP_B$ | 1.13 | 1.93 | 2.57 | 2.39 | 2.47 | 1.99 | 1.38 | 0.80 | 0.43 |
| $IP_C$ | 0.34 | 0.49 | 1.06 | 1.48 | 0.87 | 0.72 | 0.46 | 0.30 | 0.16 |

Total: 40.13

Figure 5:
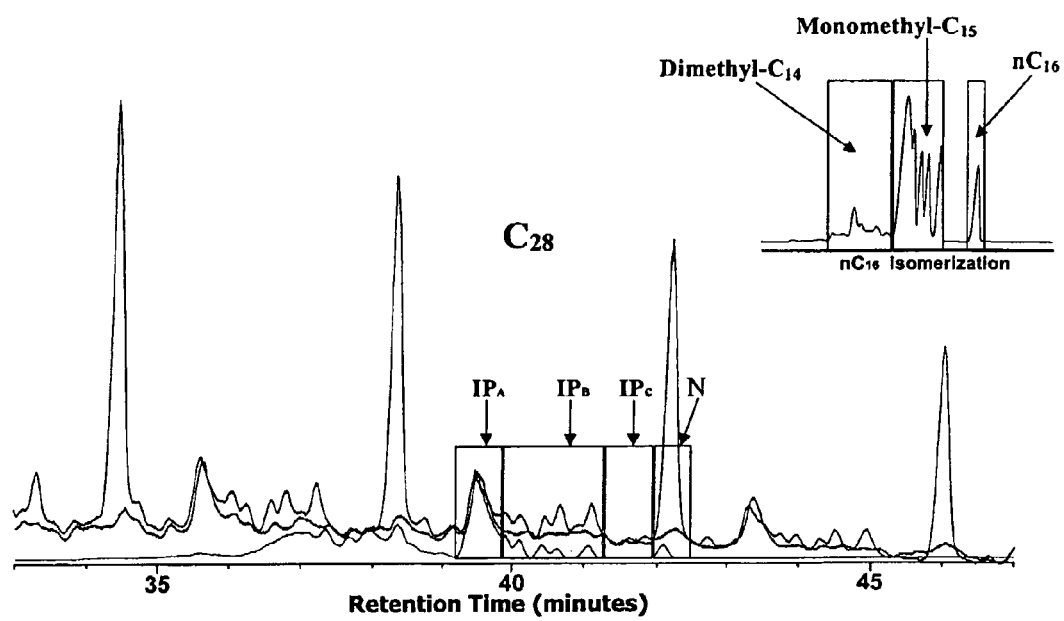
FIG. 5 is a plot of GC chromatograms showing GC retention time derived from isomerization products from a commercial feed, model compounds hexadecane ($nC_{16}$) and octaeicosane ($nC_{28}$), all over Pt/ZSM-48 catalyst.

FIG. 5 shows GC chromatograms illustrating the identifications of n-paraffin, $IP_A$, $IP_B$, and $IP_C$ regions using model compound $nC_{16}$ and $nC_{28}$ paraffins. The lowest chromatogram is from the isomerization products of nC$_{28}$ model compound, the middle chromatogram is from a commercial basestock and the upper chromatogram is for a 130N lube raffinate. The inserted chromatogram on the right hand corner is from the isomerization products of nC$_{16}$ model compound.

Based on the GC retention time derived from isomerization products using model compound hexadecane (nC$_{16}$) and octaicosane (nC$_{28}$) over Pt/ZSM-48 catalyst (shown in FIG. 5), we identified that the major components in the IP$_A$ region were identified as mono-methyl isomers of the corresponding carbon number species. The IP$_B$ region contained the mixture of mono-methyl of the corresponding carbon number species and di-methyl isomers of one carbon number above the corresponding carbon number species. The IP$_C$ region consisted di-methyl isomers of one carbon number above the corresponding carbon number species.

Figure 6:
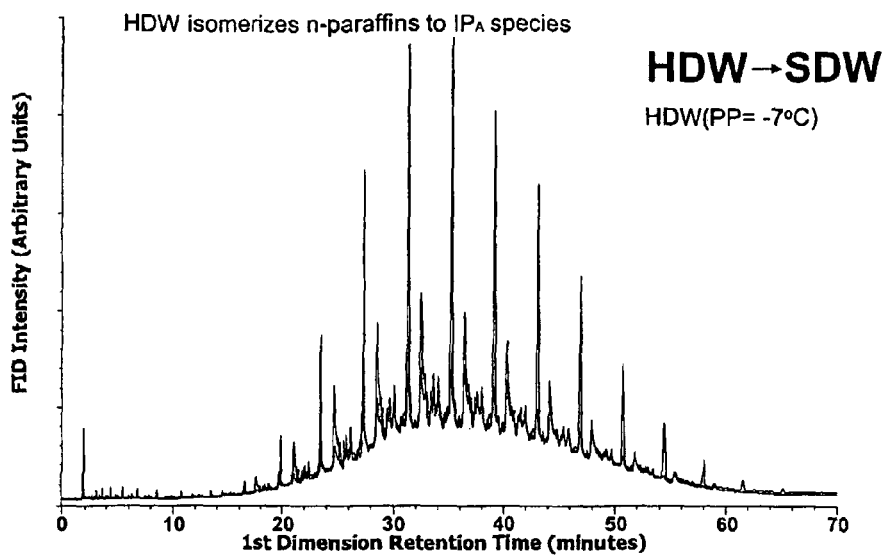
FIG. 6 shows GC chromatograms illustrating the compositional changes in n-paraffin, $IP_A$, $IP_B$, and $IP_C$ regions for HDW->SDW sample.
Figure 6:
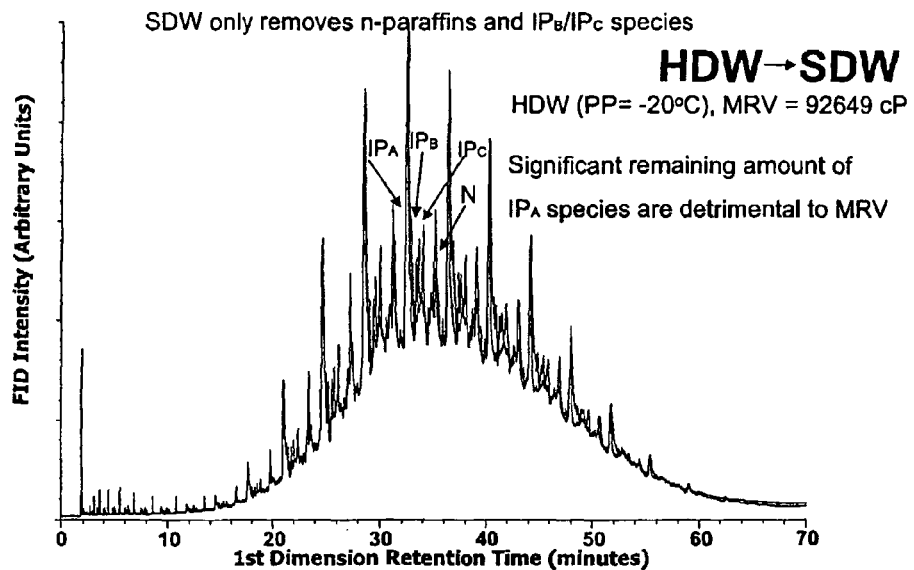

FIG. 6 shows GC chromatograms illustrating the compositional changes in n-paraffin, IP$_A$, IP$_B$, and IP$_C$ regions for HDW->SDW sample. Table 8-10 summarize the detailed molecular composition of feed and product at each process stage. Table 8 shows 130N lube Raffinate: n-Paraffins and iso-paraffins distribution based on the carbon number. Table 9 shows the HDW intermediate: paraffins and iso-paraffins distribution based on carbon number. Table 10 shows the HDW->SDW product: n-Paraffins and iso-paraffins distribution based on the carbon number.

Significantly poor MRV performance was observed for the engine oils formulated with the basestocks dewaxed through HDW→SDW versus SDW→HDW. In this HDW→SDW product, the 130N lube raffinate was HDW to −7° C. followed by SDW to −20° C., which is a very similar pour point to the trim HDW case. The 5W-30 MRV viscosity was 92,649 cP, much higher than that of the trim HDW baseoil. Thus this formulated oil fails the MRV specifications.

The first HDW step homogeneously isomerized the waxy n-paraffins to produce isomers preferentially with monomethyl substitution. The sequential SDW step only effectively removed n-paraffins. A significant amount of monomethyl isomer molecules (concentrated in IP$_A$ region) left behind in the intermediate pour point product was not effectively removed in the second SDW step due to a lower crystallization temperature (See FIG. 6).

These partially HDW molecules might impose greater difficulties for the SDW process to effectively reduce MRV in the equivalent pour point products. Therefore, the significant remaining amount of mono-methyl species were detrimental to MRV. The HDW->SDW sample presented a slightly higher paraffin content (42.68% wt) than that in the SDW->HDW sample (40.13% wt).

TABLE 8

130N Lube Raffinate
PP = 30° C.
MRV = N/A

| Carbon Number | 23 | 24 | 25 | 26 | 27 | 28 | 29 | 30 | 31 |
|---|---|---|---|---|---|---|---|---|---|
| N | 0.98 | 2.10 | 3.58 | 3.66 | 3.36 | 2.60 | 1.89 | 1.11 | 0.57 |
| IP$_A$ | 0.16 | 0.47 | 1.33 | 1.70 | 1.86 | 1.52 | 1.18 | 0.88 | 0.57 |
| IP$_B$ | 0.31 | 0.85 | 1.61 | 1.82 | 1.70 | 1.50 | 1.18 | 0.75 | 0.35 |
| IP$_C$ | 0.08 | 0.16 | 0.38 | 0.44 | 0.35 | 0.40 | 0.27 | 0.16 | 0.06 |
| | | | | | | | | Total: | 41.88 |

TABLE 9

HDW
PP = −7° C.
MRV = N/A
Rxn Temp: 300° C.

| Carbon Number | 23 | 24 | 25 | 26 | 27 | 28 | 29 | 30 | 31 |
|---|---|---|---|---|---|---|---|---|---|
| N | 0.54 | 1.14 | 1.54 | 1.34 | 1.42 | 1.06 | 0.63 | 0.43 | 0.23 |
| IP$_A$ | 0.68 | 1.61 | 2.71 | 3.26 | 3.07 | 2.48 | 1.80 | 1.29 | 0.67 |
| IP$_B$ | 0.76 | 1.58 | 2.45 | 2.59 | 2.74 | 2.33 | 1.66 | 1.00 | 0.56 |
| IP$_C$ | 0.21 | 0.48 | 0.95 | 1.39 | 0.88 | 0.77 | 0.53 | 0.35 | 0.20 |
| | | | | | | | | Total: | 47.30 |

TABLE 10

HDW → SDW
PP = 20° C.
MRV = 92649 cP

| Carbon Number | 23 | 24 | 25 | 26 | 27 | 28 | 29 | 30 | 31 |
|---|---|---|---|---|---|---|---|---|---|
| N | 0.46 | 0.98 | 1.33 | 1.13 | 1.26 | 0.91 | 0.50 | 0.35 | 0.19 |
| IP$_A$ | 0.77 | 1.73 | 2.81 | 3.16 | 2.92 | 2.23 | 1.57 | 0.99 | 0.54 |
| IP$_B$ | 0.76 | 1.45 | 2.14 | 2.09 | 2.23 | 1.85 | 1.31 | 0.76 | 0.43 |
| IP$_C$ | 0.23 | 0.46 | 1.00 | 1.47 | 0.91 | 0.77 | 0.50 | 0.33 | 0.18 |
| | | | | | | | | Total: | 42.68 |

If a comparison is made among basestock products illustrated in Table 4, Table 7 and Table 10, the calculated Isoparaffin Index (based on Equation 1) for trim HDW basestock product in Table 4 is 8.84/(10.99+4.41)=0.57 (MRV=19536 cP). The calculated Isoparaffin Index for SDW->HDW basestock product in Table 7 is 11.43/(15.09+5.88)=0.55 (MRV=37257 cP). while the Isoparaffin Index for HDW->SDW basestock product in Table 10 is 16.72/(13.02+5.84)=0.89 (MRV=92649 cP). Based on these results, it can be seen that the MRV for trim HDW basestock in Table 4 would produce a lower value than that for SDW->HDW basestock product in Table 7 and for HDW->SDW basestock product in Table 10.

The invention claimed is:

1. A process for predicting the Mini Rotary Viscometer (MRV) properties of formulated oils based on paraffin distribution which comprises:
   (a) injecting a basestock sample into a first column of a 2-dimensional gas chromatograph, said first column being coated with a non-polar material to separate the basestock sample into a series of first dimension sample components having a first set of retention times;
   (b) injecting the separated first dimension sample components from step (a) into a second column coated with a semi-polar material to further separate the separated first dimension sample components into second dimension sample components having a second set of retention times;
   (c) subjecting the first and second sets of retention times to qualitative analysis to identify iso-paraffin components or groupings thereof and to quantitative analysis to identify the quantity of the iso-paraffin components having carbon numbers in the lubricant basestock range;
   (d) grouping the iso-paraffin components into x groupings where x is a number from 0 to 3 for each identified individual lube paraffins in the carbon number range from 16 to 505;

(e) selecting a lower carbon number n and an upper carbon number m;
(f) identifying a first, second and third iso-paraffin group A, B and C for each individual carbon number over the range from n to m;
(g) calculating an isoparaffin Index by the formula:

$$\text{Isoparaffin Index} = \frac{\sum_{L=n}^{m}(IP_A)_L}{\sum_{L=n}^{m}(IP_B)_L + \sum_{L=n}^{m}(IP_C)_L}$$

and;
(h) comparing the calculated Isoparaffin Index to the Isoparaffin Index calculated for standard samples of known MRV wherein the standard samples Isoparaffin Index is a value of about 0.8 or less.

2. The process of claim 1 wherein the basestock has been solvent extracted, hydrotreated or extracted and hydrotreated.

3. The process of claim 1 wherein the basestock has been dewaxed.

4. The process of claim 3 wherein dewaxing is by at least one of solvent dewaxing or catalytic dewaxing.

5. The process of claim 4 wherein catalytic dewaxing is under effective dewaxing conditions.

6. The process of claim 5 wherein effective dewaxing conditions include temperatures between about 200° C. to about 400° C., pressures between about 2860 to about 20786 kPa, hydrogen treat gas rates of about 89 to about 890 m$^3$/m$^3$, and liquid hourly space velocities of about 0.1 to about 10 V/V/hr.

7. The process of claim 1 wherein the non-polar material has a polarity between 0 and 20.

8. The process of claim 1 wherein the semi-polar material has a polarity between 20 and 50.

9. The process of claim 1 wherein separated first dimension sample components are sent to a modulator.

10. The process of claim 7 wherein the non-polar material is a methyl silicon polymer.

11. The process of claim 8 wherein the semi-polar material is a methyl silicon polymer in which at least some of the methyl groups have been substituted by phenyl.

12. The process of claim 1 wherein the retention times for separated sample components from the second dimension are coupled with the retention times for sample components from the first dimension sample components to form a comprehensive 2D chromatogram.

13. The process of claim 1 wherein the iso-paraffin components are grouped into 3 groups.

14. The process of claim 1 wherein n is 23 and m is 31.

15. The process of claim 5 wherein the catalytic dewaxing uses a Pt/ZSM-48 dewaxing catalyst.

16. The process of claim 1 wherein the basestock sample may be formulated or non-formulated.

17. The process of claim 1 wherein the MRV of formulated oil for an Isoparaffin Index of 0.8 or less is 40000 cP or less.

18. The process of claim 16 wherein the formulated sample contains an additive package.

19. The process of claim 18 wherein the additive packages contains at least one component selected from dispersants, detergents, wear inhibitors, antioxidants, rust inhibitors, demulsifiers, extreme pressure agents, friction modifiers, multifunction additives, viscosity index improvers, pour point depressants, and foam inhibitors.

20. The process of claim 1 wherein x is 3.

21. The process of claim 1 wherein the formulated oils are for use in passenger car internal combustion engines.

* * * * *